United States Patent
Schierenbeck

(10) Patent No.: US 8,096,185 B2
(45) Date of Patent: Jan. 17, 2012

(54) APPARATUS FOR PERFORMING GROUND VIBRATION TESTS ON AIRPLANES

(75) Inventor: Detlef Schierenbeck, Bremen (DE)

(73) Assignee: Airbus Operations GmbH, Hamburg (DE)

( * ) Notice: Subject to any disclaimer, the term of this patent is extended or adjusted under 35 U.S.C. 154(b) by 0 days.

(21) Appl. No.: 12/955,068

(22) Filed: Nov. 29, 2010

(65) Prior Publication Data

US 2011/0071778 A1 Mar. 24, 2011

Related U.S. Application Data

(62) Division of application No. 12/107,516, filed on Apr. 22, 2008, now Pat. No. 7,856,884.

(30) Foreign Application Priority Data

Apr. 23, 2007 (DE) .......................... 10 2007 019 402

(51) Int. Cl.
  *B06B 3/00* (2006.01)
(52) U.S. Cl. .......................................... 73/663; 73/583
(58) Field of Classification Search ............... 73/663, 73/583, 665, 865.9; 248/542, 346.2; 415/13; 244/114 R; 254/45
See application file for complete search history.

(56) References Cited

U.S. PATENT DOCUMENTS

| | | | |
|---|---|---|---|
| 3,960,344 A * | 6/1976 | Dugan | 244/182 |
| 6,422,511 B1 * | 7/2002 | Kalisz | 244/114 R |
| 6,619,127 B2 * | 9/2003 | Miller et al. | 73/663 |
| 6,876,202 B2 * | 4/2005 | Morrison et al. | 324/330 |
| 7,328,622 B2 * | 2/2008 | Foss | 73/663 |
| 7,677,096 B2 * | 3/2010 | Robinson et al. | 73/170.02 |
| 7,792,614 B2 * | 9/2010 | Giazotto | 701/3 |
| 2003/0094952 A1 * | 5/2003 | Morrison et al. | 324/330 |
| 2006/0251507 A1 * | 11/2006 | Braswell et al. | 415/13 |

(Continued)

FOREIGN PATENT DOCUMENTS

EP 1326066 B1 * 6/2011

OTHER PUBLICATIONS

Fullenkrug U., Gloth G., Degener M., Lubrina P., "Ground Vibration Test on the Airbus A380-800" Foiliensatz zur: Aerospace Testing Expo 2005 Conferences. http://www.ukintpress-conferences.com/conf/aero05/open tech html.

Kehoe M. W., Freundinger L. C., Aircraft Ground Vibration Testing at the NASA Dryfen Flight Resesarch Facility-1993, NASA Techincal Memorandum 104275, Jun. 1994.

(Continued)

*Primary Examiner* — Hezron E Williams
*Assistant Examiner* — Samir M Shah
(74) *Attorney, Agent, or Firm* — Matthew B. Dernier, Esq.; Gibson & Dernier LLP

(57) ABSTRACT

The invention relates to improved methods and apparatus for performing ground vibration tests (so-called "ground vibration tests") on an airplane. In the method according to the invention, the airplane is jacked up essentially undamped ("rigidly") in conventional holding points with lifting devices. For purposes of the ground vibration test, the airplane is then excited to vibrate in a known manner using a plurality of vibration exciters, and the vibrations are acquired with a plurality of measuring transducers, in particular accelerometers. A dynamic vibration model of the airplane theoretically calculated beforehand can here be adjusted. The boundary conditions are removed during or after the ground vibration test, meaning the influence of the lifting device is "mathematically canceled out", so that the determined measured values reflect the so-called "free-free" state of the airplane, as if the airplane had actually been in free flight during the ground vibration tests.

17 Claims, 1 Drawing Sheet

U.S. PATENT DOCUMENTS

| | | | |
|---|---|---|---|
| 2007/0017293 A1* | 1/2007 | Foss | 73/663 |
| 2007/0032919 A1* | 2/2007 | Giazotto | 701/3 |
| 2008/0257051 A1* | 10/2008 | Schierenbeck | 73/663 |
| 2008/0282817 A1* | 11/2008 | Breed | 73/865.9 |
| 2011/0119041 A1* | 5/2011 | Daudet et al. | 703/2 |
| 2011/0146406 A1* | 6/2011 | Napolitano | 73/583 |

OTHER PUBLICATIONS

Office Action for Patent Application DE 102007019402.3-51 (and relevancy statement).

Office Action for related U.S. Appl. No. 12/107,516, Sep. 24, 2009.

* cited by examiner

US 8,096,185 B2

APPARATUS FOR PERFORMING GROUND VIBRATION TESTS ON AIRPLANES

CROSS REFERENCE TO RELATED APPLICATIONS

This application is a divisional of U.S. patent application Ser. No. 12/107,516, filed Apr. 22, 2008, now allowed, the entire disclosure of which is hereby incorporated by reference.

BACKGROUND

The invention relates to methods and apparatus for performing a ground vibration test in airplanes.

As one important safety regulation of air traffic controllers, all airplane prototypes must pass a so-called "ground vibration test" ("GVT"). In this "ground vibration test", which will henceforth be referred to as "ground vibration test" in the specification, the airplane or entire airplane structure standing on the ground is made to oscillate by means of exciters (so-called "exciters" or "(vibration) oscillators"). These vibration exciters exert an electromagnetic effect in particular, and are preferably attached in the area of the two wing ends, the two elevator unit ends, the rudder unit end, the aft fuselage, the nose and the engines of the airplane. The vibration exciters are able to excite the structure of the airplane to between 0 Hz and 50 Hz. The vibration amplitude of the vibrations in the fuselage structure generated in this way rarely reaches amplitudes exceeding 5 mm.

The object of the ground vibration test is to determine the vibration form and structural attenuation of the airplane in the area of the measuring transducers in the 0 Hz to 50 Hz frequency range of relevance in terms of the physics of flight. The levels of excitation produced by the electromagnetic vibration exciters are here chosen in such a way as to still be able to readily measure the affected variables and preclude mechanical damage to the integrity of the fuselage structure of the airplane.

In order to acquire the vibrations triggered in the airplane structure by the vibration exciters via measurement, up to 1,000 measuring transducers, preferably accelerometers, are arranged on the airplane for a ground vibration test.

Prior to the ground vibration test, a strictly computational vibration model of the airplane or airplane structure is generated. This theoretical dynamic vibration model of the airplane can encompass up to 10 million interacting node points, each with six degrees of freedom (three translatory and three rotational movements). The acceleration values and/or other measured values ascertained in real time during the ground vibration test are used to adjust or fine-tune the theoretical dynamic model of the airplane determined beforehand as required.

In the method known from prior art, the airplane rests on the ground during the ground vibration test, for example on its landing gear tires. In order to better decouple the airplane structure excited to undergo vibrations and the ground, the air pressure in the tires is generally reduced. It is further known to catch the landing gear of the airplane in a plurality of rubber rings or store the landing gear on air cushions on the hangar floor. The nonlinear tire damping effects must be canceled out of the determined measured values by means of complex algorithms.

SUMMARY OF THE INVENTION

The object of the invention is to provide a method for conducting the ground vibration test that can be performed with a comparatively low testing outlay.

In the method according to the invention for conducting a ground vibration test, the influence of nonlinear storage effects, e.g., tire damping effects, is eliminated.

In particular the following procedural steps are performed according to the invention:

Placing measurement transducers in the area of the airplane, keeping the airplane rigidly jacked up or in place, exciting airplane vibrations by means of vibration exciters, and measuring and evaluating the measured values obtained by the measuring transducers. The influence of the holding devices or holding points during the ground vibration test and/or following the ground vibration test is also cancelled out. Holding can take place by means of a holding device or several holding devices, which each hold or support one of the holding points. Such a holding device can be a hydraulic lift.

In another exemplary embodiment, the method according to the invention can involve the following steps:

a) Attaching a plurality of measuring transducers in the area of the airplane,
b) Rigidly holding the airplane in at least three holding points,
c) Exciting the airplane to vibrate with a plurality of vibration exciters,
d) Measuring and evaluating the measured values ascertained by the measuring transducers, and
e) Canceling out the influence of holding in the at least three holding points during the ground vibration test and/or following the ground vibration test.

The airplane can be rigidly jacked up in the holding points in particular using a corresponding number of holding devices. The holding devices can be realized in particular by hydraulic lifts, which are present most of the time anyway. According to the invention, it can here be provided in particular that each of the at least three holding points hold at least one hydraulic lift. The holding devices that hold the airplane rigidly in place or hydraulic lifts and hydraulic stamps do not achieve any decoupling of vibration between the ground and airplane. In comparison to the known method, in which the vibration test is performed on an airplane standing on the ground, and the influence of nonlinear tire damping effects is taken into account when evaluating the measured values, the nonlinear tire damping effects are completely eliminated from the measured values in the solution according to the invention. In addition, the method according to the invention makes it possible to use holding points provided on the airplane that usually are present under the airplane anyway, thereby eliminating the need for additional devices, for example rubber rings, air cushions or the like, to jack up the airplane on the floor during the ground vibration test. This significantly reduces the outlay required for performing the ground vibration test, thereby yielding both time and cost savings. At the same time, the number of devices to be provided for a ground vibration test decreases, and hence the storage outlay as well.

In addition to the above, the ground vibration test is significantly easier to numerically evaluate, since the influence of the jack acting in a rigid manner in the holding points from essentially a dynamic standpoint can be canceled out more easily than the previously to be considered, generally nonlinear damping influence of the landing gear tires and/or the rubber rings or the air cushion, for example.

According to the invention, it can be provided in particular that the measured values be acquired with accelerometers. The airplane can be excited to vibrate with a plurality of electromagnetic exciters. During the ground vibration test, the vibration model of the airplane can be adjusted to the measured values acquired by the measuring transducers. In particular, the vibration model of the airplane can be adjusted during the ground vibration test to the measured values acquired by the measuring transducers.

In the area of the airplane or airplane structure, as many as 1,000 measuring transducers, and in isolated cases even more than 1,000 measuring transducers, in particular accelerometers, are distributed over the entire aircraft for conducting the ground vibration test. The measuring transducers can here be placed on the aircraft from outside, and/or alternatively be affixed inside the airplane. In addition, the sensors present in the aircraft electronics systems can also assist in the ground vibration test.

The data provided by the measuring transducers can be evaluated with high-performance computers, at least partially in real time. It can further be provided that the calculation results be relayed to locations outside the test bench area via long-distance data transmission. In general, complete evaluation of the ground vibration test takes place only after all measuring series have been concluded.

A plurality of exciters is used to excite the airplane to vibrate, wherein in particular electromagnetic exciters can be placed, for example, in the area of the two wings, the two elevator unit ends, the aft fuselage, the fuselage body, as well as the engines and engine pods. The vibration exciters make it possible to excite vibrations with nearly any vibration forms, amplitudes and frequencies, wherein the excitation frequency range preferably ranges from 0 Hz to 50 Hz. As an alternative, piezoelectric and/or electromechanical exciters can also be used.

In one advantageous embodiment of the method, the influence of the at least three holding points on the acquired measured values is cancelled out through calculation during and/or after the ground vibration test.

If the influence of the at least three holding points is mathematically cancelled out already while conducting the test, corrections can be introduced in the test setup as required to reduce errors.

In another advantageous further development of the method, the vibration model of the airplane is adjusted during the ground vibration test to the measured values acquired by the measuring transducers. This makes it possible to improve the accuracy of model calculation based on the measured acceleration values already during the ground vibration test.

In another embodiment of the method according to the invention, the mechanical forces and accelerations acting on the lifting devices are uninterruptedly or continuously acquired during the ground vibration test using measuring transducers, in particular accelerometers and/or dynamometers. This prevents the sensitive hydraulic lifts from overloading during the course of the ground vibration test. If the sensors detect a critical overload, the electromagnetic exciters can be deactivated immediately.

BRIEF DESCRIPTION OF THE DRAWINGS

The drawing shows.

DETAILED DESCRIPTION OF THE INVENTION

Figure 1:
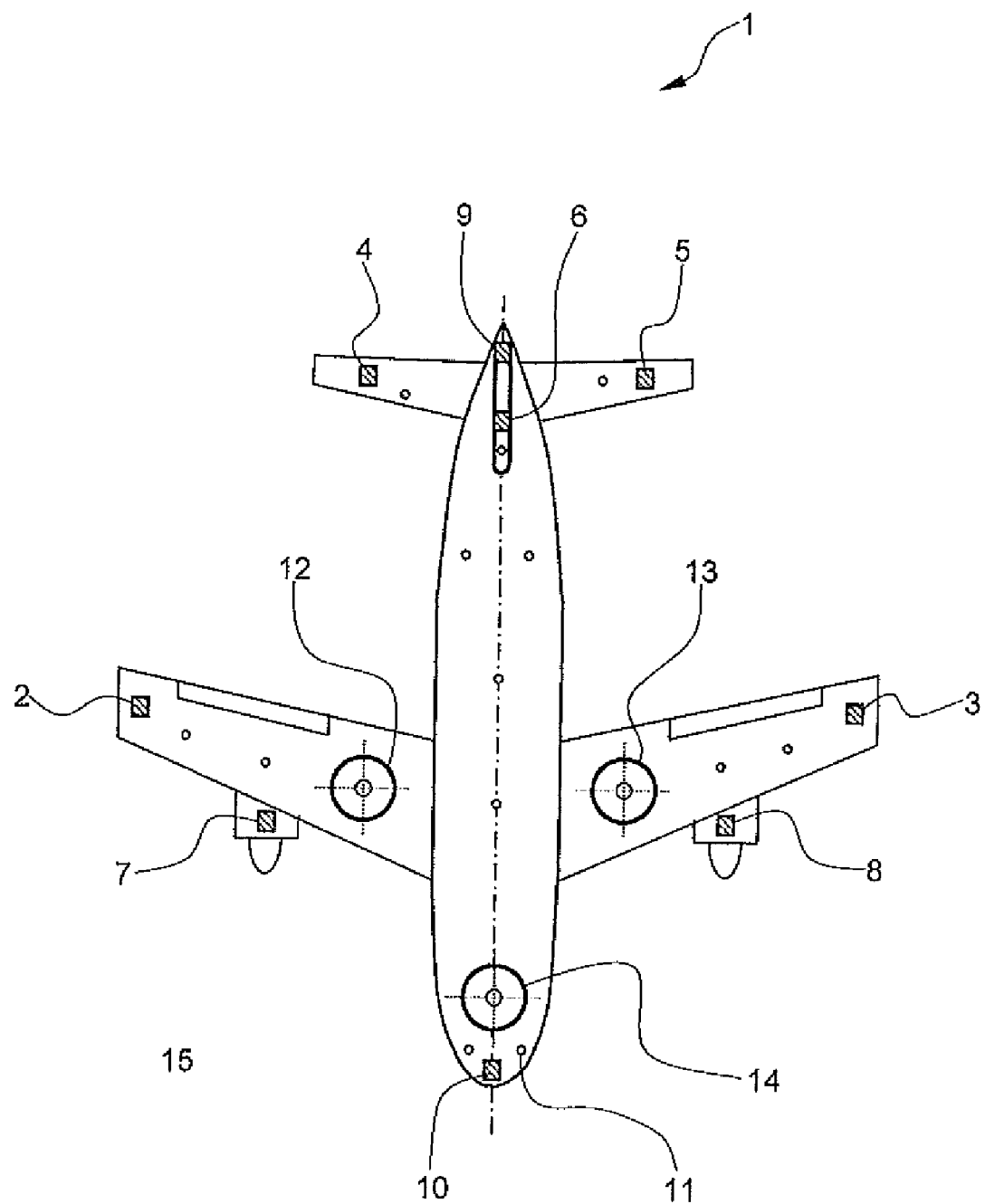
FIG. 1 A diagrammatic view of a test setup for implementing the method according to the invention.

FIG. 1 shows a top view of the test setup used for implementing the method.

The ground vibration test is performed by providing the airplane 1 or airplane structure with a plurality of vibration exciters 2 to 10. The vibration exciters can be vibration exciters with an electromagnetic and/or piezoelectric and/or electromechanical effect. In the exemplary test setup shown on FIG. 1, vibration exciters 2, 3 are arranged on the wing ends, while additional vibration exciters 4, 5 are positioned in the area of the elevator unit ends of the airplane 1. A vibration exciter 6 is arranged on the ruder unit end. To other vibration exciters 7, 8 are situated in the area of the engines, while two vibration exciters 9, 10 are located in the area of the aft fuselage and nose of the airplane 1. Fewer or more than the number of vibration exciters can also be provided at the mentioned measuring points.

The invention can provide that the vibration exciters 2 to 10 excite the fuselage structure in a frequency range of between 0 Hz and 50 Hz. The form, vibration amplitude and excitation vibration frequency are here varied with a computer. In addition, the change in set excitation frequency as a function of time can be varied over time ("wobbled"). For example, the excitation frequency generated by the vibration exciters can follow the mathematical relation sin(Omega(t)·t), meaning that the angular frequency Omega depends on time t. In addition, the airplane 1 or airplane structure incorporates a plurality of accelerometers, of which only one accelerometer 11 is provided with a reference number to provide a better illustrative overview. Depending on the size of the airplane 1, up to 1,000 accelerometers might be necessary, more than 1,000 in isolated cases. In addition, other measuring transducers can be provided, for example position measuring devices or dynamometers. The measuring transducers can be situated outside and/or inside the airplane 1. It is further possible to also use measuring transducers present in the onboard electronic system of the airplane to perform the ground vibration test.

A powerful computer or evaluator is used to acquire and evaluate the measured acceleration values provided by the accelerometers, actuate the electromagnetically acting vibration exciters 2 to 10, and acquire and evaluate the measured values provided by other measuring transducers. Prior to the ground vibration test, the construction data for the airplane 1 are used to generate a numerical vibration model for theoretically simulating the vibration behavior of the airplane. Depending on the size of the airplane 1, this vibration model can encompass in particular up to $5 \cdot 10^6$ node points each with up to six degrees of freedom, which also interact. The six degrees of freedom per node point represent the total of three translatory and three rotational movements possible for every node point. In one exemplary embodiment of the method according to the invention, the computer or evaluator has an adjustment function, with which the theoretical variation model of airplane 1 is harmonized with the measured acceleration values determined by the accelerometers during the ground vibration test performed with the method, thereby continuously improving their accuracy.

According to the invention, the airplane 1 or fuselage structure is held in several holding points (so-called "jacking points") by the holding devices (not shown on FIG. 1) during the vibration test, wherein the airplane is held in these holding points in a stable manner.

The holding devices can be realized by known hydraulic lifting devices, which jack up the airplane 1 on the ground 15. In this case, the airplane can be held in three holding points 12, 13, 14, the so-called "jacking points". Two holding points 12, 13 of these three "jacking points" are situated underneath the two wings of the airplane 1, while the third holding point 14 of the later is situated in the area underneath the nose. The three holding points 12 to 14 are arranged in such a way that the airplane 1 is roughly at equilibrium when jacked.

The holding devices provided to hold the airplane or hydraulic lifting devices 12 to 14 or hydraulic lifts used for jacking up the airplane 1 bring about a nearly "rigid" coupling between the airplane made to vibrate by the electromagnetic exciters and the ground 15, which is mathematically treated as rigid in the evaluation function implemented in the evaluator. The invention does not involve vibration decoupling between the airplane and the ground using elastic elements, for example in the form of rubber rings, air cushions, reduced air pressure in the elevator unit tires or the like. This precludes nonlinear damping effects, which otherwise would negatively influence (disrupt) the structural damping of the airplane. As a consequence, it is easier to mathematically cancel out the influence of the holding devices or lifting devices in the holding points 12 to 14.

The holding devices or lifting devices preferably each exhibit at least one dynamometer and at least one accelerometer. Position measuring devices can also be provided to enable the computer-controlled positioning of the airplane relative to the ground 15 (surface) during the ground vibration test. If prescribed (mechanical) limits are exceeded with respect to the forces and/or accelerations acting on the hydraulic lifting devices during the ground vibration test, the vibration exciters to 10, which can in particular be electromagnetic vibration exciters, can be deactivated immediately to terminate the ground vibration test.

A powerful computer with which the evaluator and controller is realized executes all of the regulation and control functions involved in the ground vibration test, including the acquisition and evaluation of measured values or acceleration values determined by the measuring transducers or accelerometers, and also actuates the vibration exciters 2 to 10. During the use of hydraulic lifting devices, the computer or evaluator and control unit can be used to position the hydraulic lifting devices. This computer also stores the numerical vibration model derived in advance from the structural data for the airplane 1, thereby already enabling a continuous harmonization between the theoretical model and currently determined acceleration values during the ground vibration test.

The invention can provide that the controller actuate the vibration exciters, and evaluate/acquire the signals sent by the measured value transducers. The numerical vibration or airplane model is to be adjusted through a comparison of setpoint and actual values. It can here be provided that the vibration excitations of the actual airplane 1 caused by the vibration exciters and acquired by the measuring transducers in a specific set of actuation commands to the vibration exciter be compared with excitations corresponding to the same set of actuation commands to the vibration exciter used to calculate the mathematical vibration model. If a difference is encountered or a maximum permissible setpoint-actual value deviation is exceeded during this setpoint-actual value comparison, an adjustment function is used to change preset parameters of the airplane model in such a way that the setpoint-actual value comparison drops below the maximum setpoint-actual value deviation value. The adjustment function can incorporate an iterative process in which a combination of parameters for the airplane model is systematically changed. The adjustment function can incorporate an iterative process in which a combination of parameters for the airplane model is systematically changed. As an alternative or in addition, the adjustment function can be based on an estimation and/or filter function used to change or optimize a predetermined set of parameters for the airplane model as a whole with a view to the required maximum deviation.

The influence of rigid holding at the holding points 12, 13, 14 can be cancelled out in the evaluator, here in particular by multiplying this influence by the acquired measured values or subtracting this influence from the acquired measured values.

In this case, the influence of rigidly holding, i.e., a simple rigid holding model, can be determined beforehand through testing and/or mathematical calculation, and stored in the evaluator. This model can then be used to multiply the influences or influencing factors possibly depending on the excitations by the determined excitations, or subtract influencing values from the determined excitations.

In an exemplary embodiment of the method according to the invention, the airplane 1 is incorporated undamped ("rigidly") in the at least three holding points 12, 13, 14 with hydraulic lifts during the vibration test of the ground 15, lifted and held in this position. In the lifted position of the airplane 1, the vibration exciters 2 to 10 excite the airplane structure. The accelerations are here determined at all relevant points of the airplane 1 by means of up to 1,000 accelerometers. The boundary conditions are then removed, meaning that the influence of the hydraulic lifting devices in the three holding points 12 to 14 is mathematically cancelled out, as though the airplane were flying "freely" in the air. As a result, the acceleration values determined by the accelerometers occupy the state referred to in aerolastic as "free-free", reflecting the actual vibrations that affect a freely flying airplane. The theoretical vibration model for the airplane structure is preferably continuously adjusted during the ground vibration test.

In another exemplary embodiment of the method according to the invention, the already present holding points underneath the airplane 1 in conjunction with the known standard lifting devices are used to lift the airplane from the ground, thereby preventing the ground vibration test from being influenced by nonlinear damping effects generated by elastic coupling elements.

REFERENCE LIST

1 Airplane
2 Vibration exciter
3 Vibration exciter
4 Vibration exciter
5 Vibration exciter
6 Vibration exciter
7 Vibration exciter
8 Vibration exciter
9 Vibration exciter
10 Vibration exciter
11 Accelerometer
12 Holding point
13 Holding point
14 Holding point
15 Ground (surface for ground vibration test)

The invention claimed is:

1. A system for performing a ground vibration test on an airplane, comprising:
a plurality of vibration exciters coupled to a plurality of locations on the airplane that operate to excite the airplane to vibrate;
a plurality of measuring transducers coupled to the airplane and operating to produce a plurality of measuring values;
at least one holding device, including a hydraulic lift, that provides an undamped, and substantially rigid support for the airplane between the airplane and ground; and
a processing system comprising an evaluator that implements a predetermined, simple, rigid holding model for the substantially rigid support.

2. The system of claim 1, wherein the at least one holding device includes at least three hydraulic lifts, at least one of the hydraulic lifts operating to couple a respective one of at least three holding points on the airplane to provide the undamped, and substantially rigid support between the airplane and ground.

3. The system of claim 1, wherein the plurality of vibration exciters include electromagnetic exciters.

4. The system of claim 1, wherein the vibration exciters are positioned in at least one of wing ends, elevator unit ends, a rudder unit end, an aft fuselage, engines, and a nose of the airplane.

5. The system of claim 1, wherein the measuring transducers are arranged at at least one of on and inside the airplane.

6. The system of claim 1, wherein the plurality of measuring transducers are up to 1,000 in number.

7. The system of claim 1, wherein the measuring transducers include accelerometers.

8. The system of claim 1, wherein the processing system operates to control the vibration exciters, and receive and evaluate the plurality of measuring values from the measuring transducers.

9. The system of claim 8, wherein the processing system includes a vibration model of the airplane.

10. The system of claim 9, wherein the vibration model mathematically treats the substantially rigid support between the airplane and the ground as rigid when evaluating the plurality of measuring values from the measuring transducers.

11. The system of claim 10, wherein the processing system operates to mathematically cancel out the influence that the rigid support of the airplane has on the vibration of the airplane during the ground vibration test.

12. The system of claim 9, wherein the vibration model of the airplane encompasses up to $5 \cdot 10^6$ node points, each with 6 degrees of freedom.

13. The system of claim 12, wherein the processing system operates to adjust the vibration model of the airplane such that the vibration model is continuously harmonized with the measuring values from the measuring transducers duration the ground vibration test.

14. The system of claim 13, wherein the processing system operates to compare vibration characteristics from the measuring values duration the ground vibration test in a specific set of actuation commands to vibration characteristics corresponding to a same set of actuation commands used in formulating the vibration model.

15. The system of claim 14, wherein the processing system operates to change preset parameters of the vibration model if a difference is encountered or a maximum permissible setpoint-actual value deviation is exceeded during the comparison.

16. The system of claim 15, wherein the processing system operates to change the preset parameters of the vibration model such that the setpoint-actual value comparison falls below the maximum setpoint-actual value deviation value.

17. The system of claim 15, wherein the processing system operates to change the preset parameters of the vibration model via an iterative process.

* * * * *